United States Patent [19]
Anderson et al.

[11] Patent Number: 5,569,159
[45] Date of Patent: Oct. 29, 1996

[54] ENDOSCOPIC SLEEVE

[76] Inventors: Keven C. Anderson, 202 Houx Dr., Whiteman AFB, Mo. 65305; Craig R. Kuhns, 1017 Walnut La., Warrensburg, Mo. 64093

[21] Appl. No.: 357,657

[22] Filed: Dec. 16, 1994

[51] Int. Cl.$^6$ ........................................................ A61B 1/04
[52] U.S. Cl. ............................ 600/114; 600/121; 600/119
[58] Field of Search ...................... 206/363, 438, 206/316.1, 305, 364; 600/119, 114, 121, 122, 124, 186, 203, 29, 30, 32; 604/27, 93, 264, 277

[56] References Cited

U.S. PATENT DOCUMENTS

| | | | |
|---|---|---|---|
| 4,877,033 | 10/1989 | Seitz, Jr. ................................... | 128/4 X |
| 5,429,118 | 7/1995 | Cole et al. ................................ | 600/121 |

*Primary Examiner*—Richard J. Apley
*Assistant Examiner*—Beverly M. Flanagan
*Attorney, Agent, or Firm*—Hovey, Williams, Timmons & Collins

[57] ABSTRACT

A disposable endoscopic sleeve adapted for receiving and gripping a medical probe is provided. The endoscopic sleeve includes an elongated flexible sleeve which slides over a probe and structure for gripping the probe. The elongated flexible sleeve is formed of thin-walled corrugated synthetic resin material and presents opposed axial ends. The axial ends are connected by a hollow passageway extending between the ends. The hollow passageway presents an inside diameter slightly greater than the outside diameter of a medical probe for receiving a medical probe in the hollow passageway. When an examiner grips the sleeve, the thin-walled sleeve collapses to engage and grip the medical probe. A pair of flange members are coupled to the axial ends of the sleeve for positioning the endoscopic sleeve adjacent a patient and for preventing the sleeve from becoming contaminated by blood, body fluids, or human excrement.

3 Claims, 2 Drawing Sheets

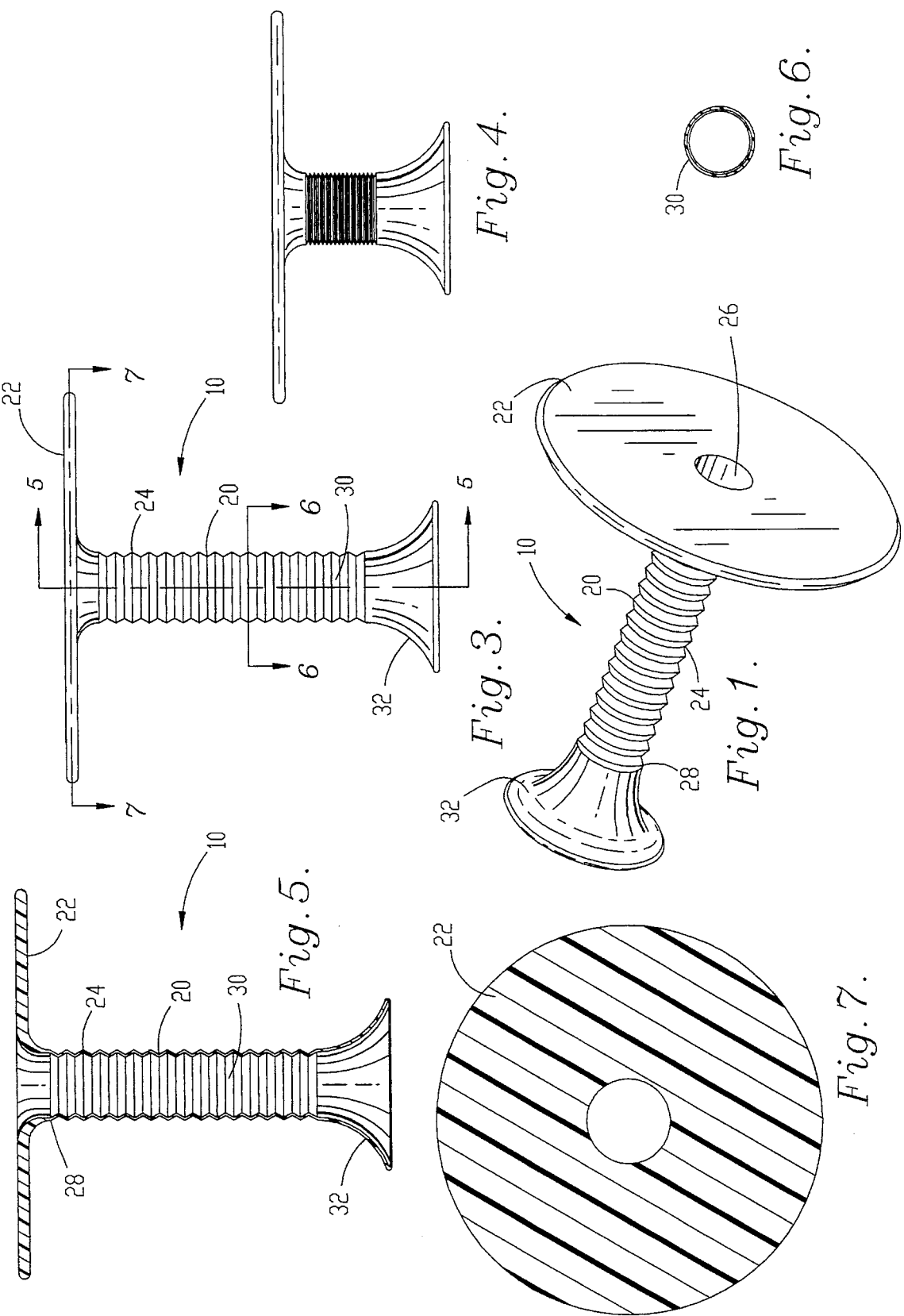

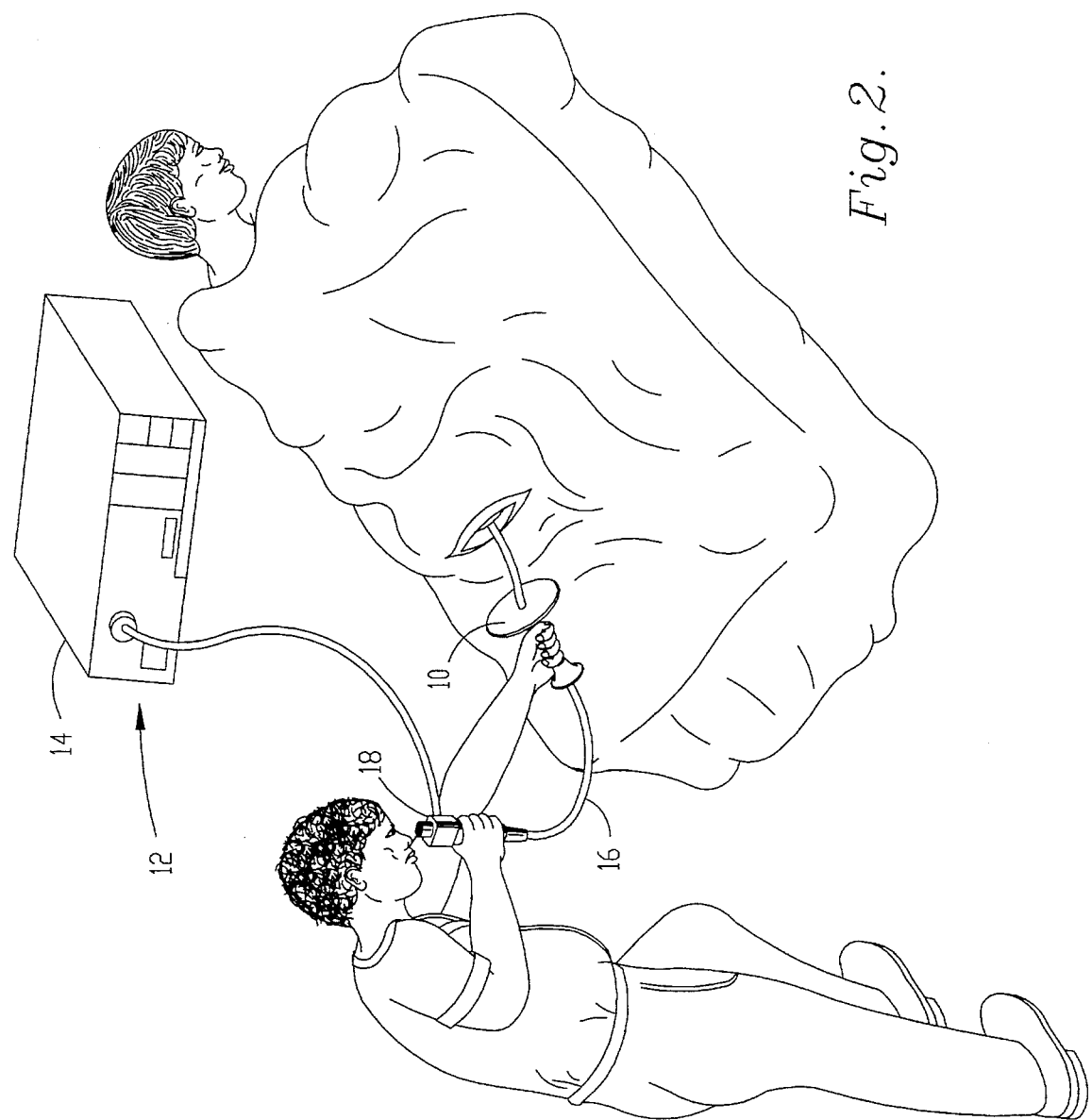

ENDOSCOPIC SLEEVE

BACKGROUND OF THE INVENTION

1. Field of the Invention

The present invention is related to devices for gripping medical probes, and more particularly to an endoscopic sleeve adapted for receiving and gripping an endoscopic probe or other type of medical probe.

2. Description of the Prior Art

Endoscopic medical devices are commonly used for inspecting the interior of an organ such as a rectum, esophagus, or urethra. These endoscopic devices typically include a light source, a flexible probe containing a light guide and small camera lens, and an eyepiece. The probe is inserted in the organ of a patient, and images of the interior of the organ are transmitted to the eyepiece or a video monitor for inspection by a medical examiner. The examiner may maneuver the probe to different portions of the organ to obtain multiple views. To reduce friction and to facilitate easy insertion and retraction, the exterior of the probe is typically coated with a lubricating gel or liquid.

The above described method of endoscopic inspection creates several difficulties for the examiner. For example, since the probe is coated with lubricating gel it is slippery and once inserted in the patient, is difficult to maneuver to different portions of the organ. The inspection method is also unsanitary because the probe often becomes coated with contaminates such as body fluids, blood and human excrements.

To improve their grip on the probe and avoid contact with these contaminants, examiners often wrap the probe with gauze or wear plastic gloves. However, the gauze quickly becomes saturated with the lubricant and contaminates the probe. The gloves further increase the slipperiness of the probe and reduce the examiner's dexterity. Also, once the examiner's gloves are contaminated, the contaminates are transferred to the probe controls during manipulation of the controls. This makes the controls difficult to operate, and directly exposes the examiner's face to the contaminates since the controls are typically located within inches of the examiner's face.

Thus, the prior art points out the need for an improved device and method for conducting endoscopic examinations which eliminates problems with the prior art.

SUMMARY OF THE INVENTION

The present invention overcomes the problems outlined above and provides a distinct advance in the state of the art. More particularly, the present invention provides a disposable endoscopic sleeve adapted for receiving and gripping a medical probe while facilitating sanitary and accurate endoscopic examination.

The preferred endoscopic sleeve broadly includes an elongated, corrugated flexible sleeve and a plurality of flange members. The elongated flexible sleeve is formed of thin-walled corrugated plastic material and presents opposed axial ends connected by a hollow passageway extending therebetween. In preferred forms, the hollow passageway presents an inside diameter slightly greater than the outside diameter of a medical probe to allow the hollow passageway to receive the medical probe. When an examiner grips the sleeve, the thin-walled sleeve collapses to engage and grip the medical probe.

The endoscopic sleeve also includes first and second flange members integrally formed with the sleeve and coupled with the opposed axial ends of the sleeve. The first flange member is formed of rigid material and is provided for positioning the endoscopic sleeve adjacent a patient. When a given distance of the medical probe is fully inserted in the patient, the first flange contacts the patient's body to act as a guide or stop. The first flange also serves as a marker to allow the examiner to determine the length of the medical probe that is inserted or retracted.

In preferred forms, the endoscopic sleeve also includes a second flange member coupled to the second axial end of the sleeve. The second flange is also integrally formed with the sleeve and is flared to engage the flared end of the endoscopic eyepiece. Both flanges are circular and have diameters greater than the diameter of the sleeve. Accordingly, when the sleeve is placed on a horizontal surface such as an examination bed, the flanges elevate the sleeve above the horizontal surface so that the sleeve remains isolated from the examination bed.

By providing this construction, numerous advantages are obtained. For example, recent OSHA standards dictate that health professionals must use or wear protective equipment that will prevent their contact with blood and/or body fluids. The present invention will reduce the chance of contact with those contaminates, thus assisting medical facilities in complying with these regulations.

The endoscopic sleeve covers the probe so that the examiner is insulated from the lubricating gel contained on the probe. To grip the probe, the examiner merely grips the sleeve and applies a slight inward force so that the walls of the sleeve collapse to engage the probe. This allows the examiner to more easily perform an endoscopic examination. The sleeve also insulates the examiner from contaminates which accumulate on the probe during examination.

Additionally, the flanges provide a convenient marker and stop for determining the length of probe inserted into or retracted from the patient. With this configuration, the examiner can more accurately pin-point certain portions of the patient's body for examination.

Additionally, the thin-walled corrugated design of the sleeve allows it to collapse along its longitudinal axis for easy shipment and storage. The sleeve is also lightweight and inexpensive, and can therefore be easily manufactured, disposed, and recycled.

BRIEF DESCRIPTION OF THE DRAWINGS

A preferred embodiment of the present invention is described in detail below with reference to the attached drawing figures, wherein:

FIG. 1 is an isometric view of a endoscopic sleeve apparatus constructed in accordance with the preferred embodiment;

FIG. 2 is a schematic view illustrating an endoscopic examination using the apparatus of FIG. 1;

FIG. 3 is a front view of the apparatus;

FIG. 4 is a front view of the apparatus shown collapsed along its longitudinal axis;

FIG. 5 is a sectional view of the apparatus taken along line 5—5 of FIG. 3;

FIG. 6 is a sectional view of the apparatus taken along line 6—6 of FIG. 3; and

FIG. 7 is a sectional view of the apparatus taken along line 7—7 of FIG. 3.

DETAILED DESCRIPTION OF THE PREFERRED EMBODIMENTS

Turning now to the drawings, and particularly FIG. 2, an endoscopic sleeve 10 constructed in accordance with the preferred embodiment is illustrated. Endoscopic sleeve 10 is designed for use with an endoscopic testing apparatus 12 such as a fiberscope manufactured by Olympus. Endoscopic testing apparatus 12 includes light source 14, flexible probe 16, and eyepiece 18. Probe 16 contains a light guide and small camera lens. As illustrated, probe 16 is inserted in a hollow organ of a patient, and images of the organ are transmitted to eyepiece 18 for inspection by an examiner. Endoscopic sleeve 10 is adapted for receiving and gripping probe 16 to facilitate sanitary and accurate endoscopic examination.

Referring to FIG. 1, endoscopic sleeve 10 broadly includes an elongated, corrugated flexible sleeve 20 and first and second flange members 22 and 32. In more detail, sleeve 20 includes sidewall 24 which presents opposed first and second axial ends 26 and 28 and hollow passageway 30 extending therebetween. Passageway 30 is adapted to receive a medical device such as an endoscopic probe and presents an inside diameter slightly greater than the outside diameter of the probe. In preferred forms, passageway 30 presents and inside diameter of approximately 15–20 millimeters and is adapted to couple with an endoscopic probe presenting an outside diameter of approximately 13 millimeters.

Sleeve 20 is preferably formed of thin-walled corrugated plastic material. The thin-walled design of sleeve 20 allows it to collapse inwardly when gripped by an examiner. Thus, sleeve 20 can be easily positioned over probe 16 and is operable to engage and grip probe 16 when subjected to a gripping force. With this configuration, endoscopic sleeve 10 slides freely over endoscopic probe 16 but engages the probe when subjected to a gripping force.

As best illustrated in FIG. 5, sidewall sleeve 20 presents a plurality of inwardly and outwardly extending ribs 24. The inwardly extending ribs provide a textured surface for engaging and gripping probe 16 when sidewall sleeve 20 is subjected to a gripping force. The outwardly extending ribs provide a textured gripping surface for improving the examiner's grip on the endoscopic sleeve 10.

Inwardly and outwardly extending ribs 24 fold along a longitudinal axis extending through passageway 30 (see FIG. 4), allowing sleeve 20 to collapse about this longitudinal axis. This collapsing movement facilitates easy storage and transport of endoscopic sleeve 10. This also allows the examiner to slide endoscopic sleeve 10 all the way back to eyepiece 18 so that endoscopic sleeve 10 collapses against the eyepiece. Accordingly, the examiner can insert nearly the entire length of probe 16 into the patient.

Although sleeve 20 is preferably formed of thin-walled synthetic resin material such as plastic, it may be formed of any flexible material. For example, flexible foam rubber or any other material which can be compressed inwardly to engage probe 16 when subjected to a gripping force by an examiner may be used. Additionally, sleeve 20 may be slit along its longitudinal axis so that it can be placed lengthwise over probe 16. The resilient and flexible nature of the sleeve material allows the sleeve to maintain its position over probe 16 without adhesives. Alternatively, the slit may be taped or glued.

Endoscopic sleeve 10 also includes first and second flange members 22 and 32 coupled to sleeve opposed first and second axial ends 26 and 28, respectively. Flange members 22 and 32 are preferably integrally formed with sleeve 20 and are made of the same synthetic resin material as sleeve 20.

First flange member 22 is generally circular in shape and rigid in structure. Flange 22 serves several purposes. First, flange 22 allows the examiner to position endoscopic sleeve 10 immediately adjacent a patient by providing a convenient stop for contacting the patient when probe 16 is fully inserted into the patient. With this configuration, an examiner can utilize nearly the full length of probe 16 without directly touching the patient. Second, flange 22 provides a convenient marker for allowing an examiner to determine the length of probe 16 inserted into or retracted from a patient. For example, if the examiner wishes to insert probe 16 two inches into the hollow organ, he can first position flange 22 two inches from the end of probe 16 or from the previous point of insertion and then insert the probe until flange 22 contacts the patient's body.

Endoscopic sleeve 10 also includes second flange member 32 coupled with second axial end 28 of sleeve 20. Flange 32 is preferably integrally formed of flexible thin-walled plastic and is flared outwardly for engaging the flared end of eyepiece 18. With this configuration, endoscopic sleeve 10 can be positioned immediately adjacent eyepiece 18 to allow the full length of scope 16 to be inserted into the patient.

Flange members 22 and 32 present diameters greater than the outside diameter of sleeve 20. Accordingly, flanges 22 and 32 cooperate to elevate sleeve 20 above a horizontal surface. Thus, when endoscopic sleeve 10 is placed on a horizontal surface such as an examination bed, sleeve 20 does not touch the examination bed. This isolates sleeve 20 from blood or body fluids which accumulates on the bed and thereby prevents it from becoming contaminated.

In operation, endoscopic sleeve 10 is adapted for receiving and gripping a medical probe such as endoscopic probe 16. Endoscopic sleeve 10 is first placed over probe 16 so that the end of probe 16 extends from flange 22. The examiner then grips sleeve 20 to collapse the sleeve sidewall until it engages the probe. The examiner can position endoscopic sleeve 10 along the length of probe 16 by releasing his grip so that the sleeve sidewall disengages the probe. For example, if the examiner wishes to insert probe 16 two inches into the patient, he positions flange 22 two inches from the end of probe 16. The examiner then grips sleeve 20 and inserts probe 16 into the patient.

If the examiner wishes to adjust the positioning of endoscopic sleeve 10 on probe 16, he releases the pressure on sleeve 20 and slides endoscopic sleeve 10 relative to probe 16. Alternatively, if the examiner wishes to maneuver probe 16 within the patient, he increases the pressure on sleeve 20 to collapse sidewall 24 on probe 16. This allows the examiner to grip probe 16 in a stationary position while maneuvering it in and out of the patient.

Flanges 22 and 32 elevate sleeve 20 above the horizontal surface of the bed and isolate it from the bed. Thus, if the examiner wishes to use both of his hands to hold eyepiece 18, he can lay endoscopic sleeve 10 on the examination bed without exposing sleeve 20 to any contaminates located on the bed. Flanges 22 and 32 also allow the examiner to easily grasp the sleeve without it becoming tangled in the sheets on the examination bed.

Once the endoscopic examination is completed, the examiner can remove probe 16 from the patient, slide endoscopic sleeve 10 off of probe 16, and dispose of endoscopic sleeve 10 without ever touching probe 16. This allows the examiner to perform the entire endoscopic examination in a clean and sanitary fashion.

Although the invention has been described with reference to the preferred embodiment illustrated in the attached drawing figures, it is noted that equivalents may be employed and substitutions made herein without departing from the scope of the invention as recited in the claims. For example, the sleeve of the endoscopic sleeve may be formed of any flexible material which collapses inwardly when gripped. Additionally, the flange members may be formed in a variety of shapes and sizes.

Having thus described the preferred embodiments of the present invention, what is claimed as new and desired to be protected by Letters patent includes the following:

1. An endoscopic sleeve device adapted for receiving and gripping a medical probe, comprising:

an elongated flexible endoscopic sleeve including a sidewall presenting opposed axial ends and a hollow passageway extending between said axial ends;

said endoscopic sleeve including structure sized and configured for engaging and gripping a medical probe received in said passageway when said sleeve is gripped;

a flange member coupled to one of said axial ends for positioning said endoscopic sleeve adjacent a patient; and a second flange member coupled to the other of said axial ends for positioning said endoscopic sleeve adjacent a medical probe eyepiece.

2. An endoscopic sleeve device adapted for receiving and gripping a medical probe, comprising:

an elongated flexible endoscopic sleeve including a sidewall presenting opposed axial ends and a hollow passageway extending between said axial ends;

said endoscopic sleeve including structure sized and configured for engaging and gripping a medical probe received in said passageway when said sleeve is gripped, said structure including a plurality of inwardly extending ribs;

said endoscopic sleeve further including a plurality of outwardly extending ribs for providing a gripping surface for handling said endoscopic sleeve;

wherein said inwardly and outwardly extending ribs are configured for folding along a longitudinal axis extending through said endoscopic sleeve passageway to collapse said endoscopic sleeve.

3. The apparatus as set forth in claim 1, wherein said flange member and said second flange member present diameters greater than the diameter of said sleeve whereby said flange member and said second flange member cooperate to elevate said sleeve above a horizontal surface to prevent said sleeve from contacting the horizontal surface.

* * * * *